(12) United States Patent
Nash

(10) Patent No.: US 11,020,163 B2
(45) Date of Patent: *Jun. 1, 2021

(54) CRYOGENIC KYPHOPLASTY INSTRUMENT AND METHODS OF USE

(71) Applicant: Medtronic Holding Company Sàrl, Tolochenaz (CH)

(72) Inventor: Stephen Nash, Galway (IE)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 431 days.

This patent is subject to a terminal disclaimer.

(21) Appl. No.: 15/921,049

(22) Filed: Mar. 14, 2018

(65) Prior Publication Data

US 2018/0199977 A1 Jul. 19, 2018

Related U.S. Application Data

(63) Continuation of application No. 14/288,437, filed on May 28, 2014, now Pat. No. 9,936,997.

(51) Int. Cl.
*A61B 18/02* (2006.01)
*A61B 18/00* (2006.01)
*A61B 90/00* (2016.01)

(52) U.S. Cl.
CPC ...... *A61B 18/02* (2013.01); *A61B 2018/0022* (2013.01); *A61B 2018/00041* (2013.01); *A61B 2018/00339* (2013.01); *A61B 2018/00577* (2013.01); *A61B 2018/00791* (2013.01); *A61B 2018/0293* (2013.01); *A61B 2090/064* (2016.02)

(58) Field of Classification Search
CPC ................ A61B 17/8855; A61B 18/02; A61B 2018/00041; A61B 2018/0022; A61B 2018/00339; A61B 2018/00577; A61B 2018/00791; A61B 2018/0293; A61B 2090/064
USPC ...................................................... 606/20–26
See application file for complete search history.

(56) References Cited

U.S. PATENT DOCUMENTS

| 6,989,009 | B2 | 1/2006 | Lafontaine |
| 7,189,227 | B2 | 3/2007 | Lafontaine |
| 8,425,507 | B2 | 4/2013 | Pellegrino et al. |
| 8,574,225 | B2 | 11/2013 | Reynolds et al. |

(Continued)

*Primary Examiner* — Michael F Peffley
*Assistant Examiner* — Khadijeh A Vahdat
(74) *Attorney, Agent, or Firm* — Sorell, Lenna & Schmidt, LLP

(57) ABSTRACT

A surgical instrument includes an outer shaft defining a passageway. An inner shaft is disposed within the passageway and defines a lumen. An expandable structure has a first end coupled to a second end of the outer shaft and a second end coupled to a second end of the inner shaft. The expandable member defines a chamber. A delivery shaft includes a first end positioned within the passageway and a second end positioned within the chamber. The delivery shaft defines a channel configured to deliver a coolant out of an opening in the second end of the delivery shaft and into the chamber to move the expandable structure from an unexpanded configuration to an expanded configuration. A variable exhaust valve is in communication with the passageway and is configured to regulate pressure within the chamber. Systems and methods are disclosed.

14 Claims, 3 Drawing Sheets

(56) References Cited

U.S. PATENT DOCUMENTS

| | | | |
|---|---|---|---|
| 2004/0243119 A1* | 12/2004 | Lane | A61B 18/02 606/21 |
| 2007/0233249 A1 | 10/2007 | Shadduck | |
| 2007/0299433 A1 | 12/2007 | Williams et al. | |
| 2011/0184398 A1 | 7/2011 | Desrochers | |
| 2013/0006256 A1 | 1/2013 | Paul et al. | |
| 2013/0110098 A1 | 5/2013 | Lalonde | |

* cited by examiner

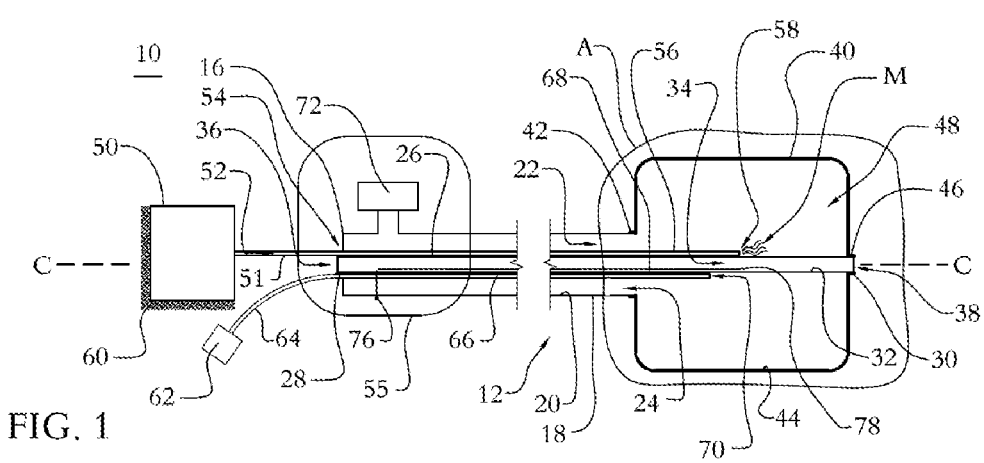
FIG. 1
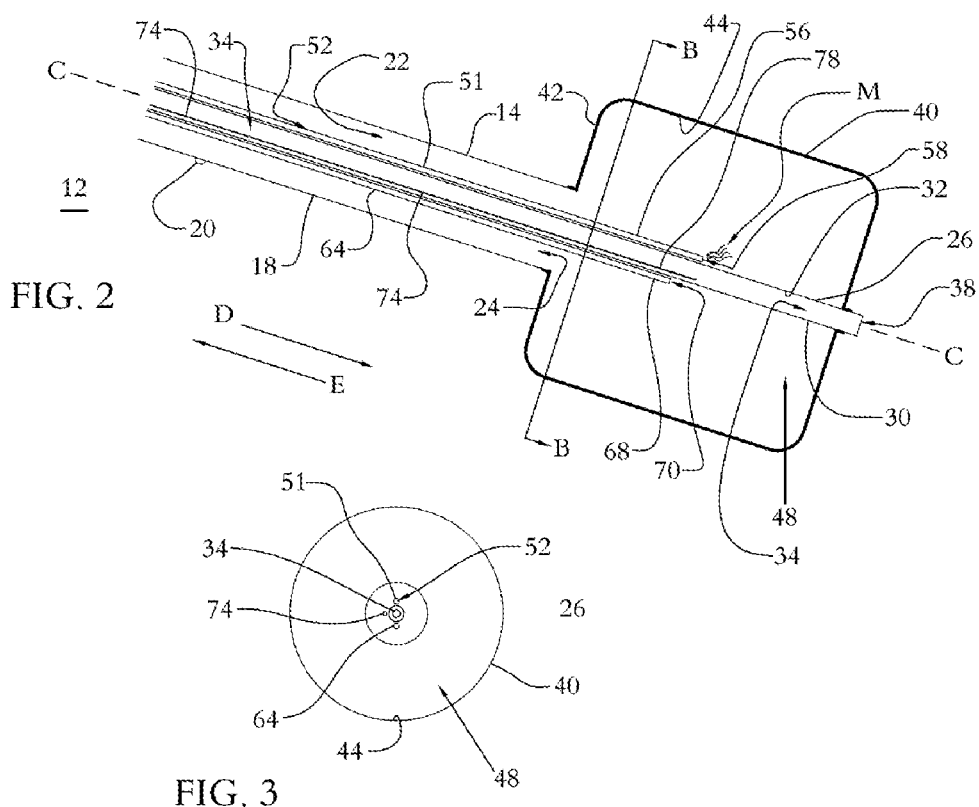
FIG. 2
FIG. 3

CRYOGENIC KYPHOPLASTY INSTRUMENT AND METHODS OF USE

CROSS-REFERENCE TO RELATED APPLICATIONS

This application is a continuation of application U.S. patent application Ser. No. 14/288,437, filed on May 28, 2014, now U.S. Pat. No. 9,936,997, which is hereby incorporated by reference herein, in its entirety.

TECHNICAL FIELD

The present disclosure generally relates to medical devices for the treatment of musculoskeletal disorders, and more particularly to a surgical system and method to facilitate treatment while minimizing pain.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

In an effort to more effectively and directly treat vertebral compression fractures, minimally invasive techniques such as vertebroplasty and, subsequently, kyphoplasty, have been developed. Vertebroplasty involves creating a cavity in a fractured, weakened, or diseased vertebral body. A flowable reinforcing material, usually polymethylmethacrylate (PMMA—commonly known as bone cement), is injected into the cavity. Shortly after injection, the liquid filling material hardens or polymerizes, desirably supporting the vertebral body internally, alleviating pain and preventing further collapse of the injected vertebral body. However, creating the cavity in the fractured, weakened, or diseased vertebral body may involve pain, if untreated.

Traditional cryogenic systems, such as, for example, cryoablation systems can provide denervation capabilities, but the procedures can take a considerable amount of time to perform. Another problem with currently available cryoablation devices is that they are not cost effective. Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue. This disclosure describes an improvement over these prior art technologies.

SUMMARY

In one embodiment, a surgical instrument is provided. The surgical instrument comprises an outer shaft extending along a longitudinal axis between a first end and an opposite second end. The outer shaft comprises an inner surface defining a passageway. An inner shaft is disposed within the passageway. The inner shaft extends between a first end and an opposite second end. The inner shaft comprises an inner surface defining a lumen. An expandable structure has a first end coupled to the second end of the outer shaft and an opposite second end coupled to the second end of the inner shaft. The expandable member comprises an inner surface defining a chamber. A delivery shaft comprises a first end positioned within the passageway and a second end positioned within the chamber. The delivery shaft comprises an inner surface defining a channel configured to deliver a coolant out of an opening in the second end of the delivery shaft and into the chamber to move the expandable structure from an unexpanded configuration to an expanded configuration. A variable exhaust valve is in communication with the passageway and is configured to regulate pressure within the chamber. In some embodiments, systems and methods are provided.

BRIEF DESCRIPTION OF THE DRAWINGS

The present disclosure will become more readily apparent from the specific description accompanied by the following drawings, in which:

FIG. 1 is a side, cross sectional view of components of one embodiment of a surgical system in accordance with the principles of the present disclosure;

FIG. 2 is a cross sectional view of components shown in FIG. 1, taken at Detail A in FIG. 1;

FIG. 3 is a cross sectional view of components shown in FIG. 1 taken along lines B-B in FIG. 2;

DETAILED DESCRIPTION

Figures 4, 5:
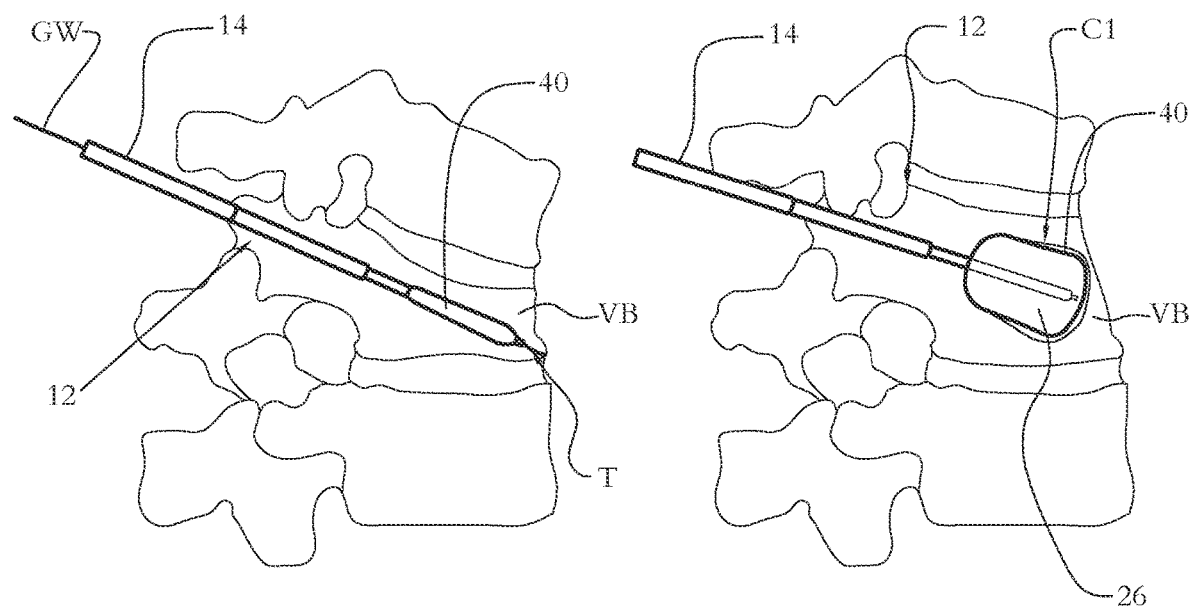
FIG. 4 is a plan view of components shown in FIG. 1, used in connection with a surgical procedure.
FIG. 5 is a plan view of components shown in FIG. 1, used in connection with a surgical procedure.

The exemplary embodiments of a surgical system and related methods of use disclosed are discussed in terms of medical devices for the treatment of musculoskeletal disorders and more particularly, in terms of a surgical system and method to facilitate treatment while minimizing pain. In one embodiment, the surgical system includes a surgical instrument that reduces pain associated with a surgical procedure, such as, for example, a kyphoplasty procedure. In some embodiments, the instrument includes a Cryo balloon that is filled and/or inflated using a coolant, such as, for example nitrous oxide ($N_2O$). In some embodiments, the instrument is configured to deform tissue, such as, for example, create a cavity in cancellous bone. Cryo energy is delivered to surrounding tissue to lessen pain associated with the procedure. In some embodiments, the Cryo energy is delivered at the same time the cavity is created. Once the Cryo energy denervates surrounding nerves, the cavity is filled with a material, such as, for example, bone cement. In some embodiments, one balloon is used to create the cavity. The balloon is removed and another balloon is inserted into the cavity that emits Cryo energy to nerves surrounding the balloon. Once the Cryo energy denervates surrounding nerves, the cavity is filled with a material, such as, for example, bone cement. In some embodiments, denervation has pain benefits to the overall spinal pain. In some embodiments, denervation decreases pain associated with the procedure. In some embodiments, denervation slows the progression of the compressions.

In some embodiments, a narrow pathway is made into fractured bone using a hollow instrument. A small orthopaedic balloon is guided through the instrument into the vertebral body. In some embodiments, the incision site is approximately 1 cm (⅓ inch) in length. In some embodiments, two balloons are used, one on each side of the vertebral body, to better support the bone as it moves back into position and increase the likelihood of deformity correction. In some embodiments, the instrument includes a balloon capable of very high internal pressures, such as, for example, pressures equal to or greater than about 400 psi. These high pressures are required to form a cavity in bone. The cavity provides space for bone cement. The balloons are carefully inflated in an attempt to raise the collapsed vertebral body and return it to its normal position. In some embodiment, a coolant such as, for example, nitrous oxide is used to fill at least one of the balloons. In some embodiments, the coolant is delivered into the balloon as a liquid. Once it enters the balloon, the liquid goes from an area of high pressure (inside the coolant lumen) to low pressure (in the balloon chamber). This pressure gradient cause the liquid to evaporate to a gas, thus inflating the balloon. The larger the pressure drop, the colder the temperature. The balloon pressure can be controlled by a pressure regulator and also the balloon outer diameter can be controlled by the balloon pressure. Inflation of the balloons creates a cavity (space) within the vertebral body that compacts the soft, inner bone against the outer wall. The cavity also functions as a "container" for tile bone cement. Once the vertebral body is in the correct position, the balloons are deflated and removed. In some embodiments, the pressure within the balloons is reduced prior to deflating and/or removing the balloons. In some embodiments, the pressure within the balloons is reduced via a variable exhaust valve. As the nitrous oxide transitions from a liquid to a gas, the nitrous oxide creates cold energy that denervates surrounding nerves. Following denervation, the balloon(s) is/are removed and the cavity is filled with thick bone cement to stabilize the fracture. The bone cement forms an internal cast that holds the vertebral body in place.

In some embodiments, the instrument includes a balloon capable of very high internal pressures, such as, for example, pressures equal to or greater than about 400 psi. In some embodiments, the instrument includes a balloon capable of very high internal pressures, such as, for example, pressures equal to or greater than about 700 psi. This allows nitrous oxide to be delivered into the balloon under significant pressure such that the balloon creates a cavity in bone. Pressure within the balloon is decreased via a variable exhaust valve. In some embodiments, the pressure is reduced to between about 5 and about 25 psi to create cold energy that denervates nerves surrounding the balloon. In some embodiments, the balloon is a single wall balloon to allow for efficient energy transfer of the cold energy created by the pressure reduction within the balloon on the nitrous oxide. In some embodiments, the nitrous oxide transitions from a liquid to a gas as a result of the pressure reduction within the balloon. In some embodiments, exhaust gas is provisionally stored in a handle of the instrument, but does not exit the system until it reaches a threshold set by the system. In some embodiments, the threshold is high for kyphoplasty and is low for denervation. In some embodiments, the instrument includes a control system that can toggle between high and low pressure to create a cavity and then denervate the nerves. In some embodiments, the entire system can be controlled by a console. In some embodiments, the entire system can be controlled by a smart handle.

In some embodiments, feedback on temperatures and balloon pressure is monitored for controlled kyphoplasty/denervation.

In some embodiments, the balloon can be inflated incrementally with pressure to control the balloon outer diameter and thus control the creation of the cavity. This can start at a low pressure of about 50 psi and rise gradually to about 400 psi. In some embodiments, the balloon is inflated to have an internal pressure of about 50 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 100 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 150 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 200 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 250 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 300 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 350 psi to create a cavity within bone and the pressure within the balloon is reduced to about 10 psi to cause the nitrous oxide to transition from liquid to gas to create cold energy to denervate nerves within the bone. In some embodiments, the balloon is inflated to have an internal pressure of about 400 psi to create a cavity within bone and the pressure within the balloon is reduced to about 10 psi to cause the nitrous oxide to transition from liquid to gas to create cold energy to denervate nerves within the bone.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-9, there are illustrated components of a surgical system 10 including a surgical device, such as, for example, a surgical instrument 12 in accordance with the principles of the present disclosure.

The components of surgical system 10 can be fabricated from biologically acceptable materials suitable for medical applications, including metals, synthetic polymers, ceramics and bone material and/or their composites, depending on the particular application and/or preference of a medical practitioner. For example, the components of surgical system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Instrument 12 comprises an outer shaft 14 extending along a longitudinal axis C between an end 16 and an opposite end 18. Shaft 14 has a length defined by the distance between ends 16, 18. In some embodiments, shaft 14 has a uniform width and/or diameter along the entire length of shaft 14. Shaft 14 comprises an inner surface 20 defining a passageway 22 having a cylindrical cross sectional configuration. End 18 comprises a circular opening 24 that is in communication with passageway 22. Opening 24 is coaxial with axis C. Passageway 22 has a length defined by the length of shaft 14. In some embodiments, passageway 22 has a uniform width and/or diameter along the entire length of passageway 22. In some embodiments, shaft 14 comprises a flexible material such that shaft 14 can bend without breaking. In some embodiments, shaft 14 comprises a rigid material such that shaft 14 cannot bend without breaking. In some embodiments, at least a portion of shaft 14 is transparent or translucent to permit visualization of components within passageway 22. In some embodiments, passageway 22 and/or opening 24 may have various cross section configurations, such as, for example, oval, oblong, triangular, rectangular, square, polygonal, irregular, uniform, non-uniform, variable, tubular and/or tapered. In some embodiments, opening 24 may be disposed at alternate orientations, relative to axis C, such as, for example, transverse, perpendicular and/or other angular orientations such as acute or obtuse, co-axial and/or may be offset or staggered.

An inner shaft 26 is disposed within passageway 22 such that shaft 26 is coaxial with axis C. Shaft 26 extends between an end 28 and an opposite end 30. Shaft 26 has a length defined by the distance between ends 28, 30. In some embodiments, shaft 26 has a uniform width and/or diameter along the entire length of shaft 26. Shaft 26 comprises an inner surface 32 defining a lumen 34 having a cylindrical cross sectional configuration. Lumen 34 has a length defined by the length of shaft 26. In some embodiments, lumen 34 has a uniform width and/or diameter along the entire length of lumen 34. In some embodiments, shaft 26 comprises a flexible material such that shaft 26 can bend without breaking. In some embodiments, shaft 26 comprises a rigid material such that shaft 26 cannot bend without breaking. In some embodiments, at least a portion of shaft 26 is transparent or translucent to permit visualization of components within lumen 34. In some embodiments, end 28 includes a circular aperture 36 an end 30 comprises a circular aperture 38. Apertures 36, 38 are in communication with lumen 34 such that a component, such as, for example, a guide wire can be inserted into aperture 36 and be positioned such that an end of the guide wire extends through aperture 38. Apertures 36, 38 are each coaxial with axis C. In some embodiments, end 30 comprises an end surface extending perpendicular to axis C such that end 30 is closed. In some embodiments, lumen 34, aperture 36 and/or aperture 38 may have various cross section configurations, such as, for example, oval, oblong, triangular, rectangular, square, polygonal, irregular, uniform, non-uniform, variable, tubular and/or tapered. In some embodiments, lumen 34, aperture 36 and/or aperture 38 may be disposed at alternate orientations, relative to axis C, such as, for example, transverse, perpendicular and/or other angular orientations such as acute or obtuse, co-axial and/or may be offset or staggered. In some embodiments, shaft 26 is rotatably and/or slidably disposed within passageway 26. In some embodiments, shaft 26 is fixed relative to shaft 14. For example, in one embodiment, end 28 extends through an opening 54 in end 16 and is fixed to a handle 55. End 16 is also fixed to handle 55 to fix shaft 26 relative to shaft 14. In some embodiments, handle 55 is an ergonomic handle configured to be gripped by hand by a medical practitioner.

An expandable structure, such as, for example, a balloon 40 comprises an end 42 coupled to end 18 such that an inner surface 44 of balloon 40 engages an outer surface of shaft 14 and an opposite end 44 coupled to end 30 such that surface 44 engages an outer surface of shaft 26. In some embodiments, balloon 40 is attached to shafts 14, 26 by adhesive bonding, thermal bonding, laser bonding, or RF bonding. Surface 44 defines a chamber 48 configured for disposal of a material to increase pressure within chamber 48 to move balloon 40 from an unexpanded or collapsed orientation, as shown in FIG. 4, to an expanded or inflated orientation, as shown in FIG. 5. In some embodiments, balloon 40 is a single wall balloon made from a compliant material. In some embodiments, balloon 40 comprises a thin, single layer of material configured to permit the transfer of energy, such as, for example, cold and/or Cryo energy through the balloon wall. In some embodiments, a tip of shaft 26 extends beyond end 46, as shown in FIG. 1. In some embodiments, the tip of shaft is flush with end 46, as shown in FIG. 2. In some embodiments, balloon 40 comprises various compliant and/or non-compliant materials, for example, latex and/or polyethylene terephthalate (PET), polyurethane, nylon or polyether block amide. Other materials are also contemplated. In some embodiments, at least a portion of balloon 40 comprises a transparent or translucent material to facilitate visualization of components disposed within chamber 48. In some embodiments, the shapes and sizes of balloon 40 when in the expanded orientation can be selected to provide a desired result during a procedure. For example, balloon 40 may include shapes such as spheres, cylinders, multi-lobed shapes, etc. and have different dimensions to make balloon 40 narrower or wider in a longitudinal direction, or extend further in a radial direction, etc.

Chamber 48 is configured to transition between a deflated or collapsed orientation and an inflated or expanded orientation, as discussed above. Chamber 48 is shown in the expanded orientation in FIGS. 1-3, 5 and 6. Chamber 48 is shown in the collapsed orientation in FIG. 4. To move chamber 48 from the collapsed orientation to the expanded orientation, a material source, such as, for example, a coolant source 50, is coupled to instrument 12. Source 50 includes a delivery shaft 51 comprising an inner surface defining a channel, such as, for example, an inlet 52. An end of shaft 51 is directly coupled to source 50 and an opposite end 56 of shaft 51 is positioned in chamber 48. An intermediate portion of shaft 51 is positioned in passageway 22. End 56 includes an opening 58 that is in communication with inlet 52 such that a material can be delivered from source 50, through inlet 52 and exit inlet 52 through opening 58 for disposal in chamber 48. As the material is introduced into chamber 48, pressure within chamber 48 increases, causing chamber 48 to transition from the collapsed orientation to the expanded orientation. Shaft 51 and opening 58 each extend parallel to axis C and are offset from axis C. In some embodiments, shaft 51 is directly coupled to the outer surface of shaft 26 such that shaft 51 is fixed to shaft 26 and/or shaft 51 extends parallel to axis C. In some embodiments, shaft 51 is removable from shaft 26 and/or is movable relative to shaft 26. In some embodiments, source 50 comprises a heat element 60 comprising at least one heating and/or cooling element, such as, for example, a thermoelectric device configured to heat and/or cool the material stored within source 50 to adjust the temperature of the material, as selected by a medical practitioner, for example. In some embodiments, the material stored within source 50 is pressurized. In some embodiments, the material stored within source 50 comprises a pressure of at least about 50 psi. In some embodiments, the material stored within source 50 comprises a pressure of at least about 100 psi. In some embodiments, the material stored within source 50 comprises a pressure of at least about 400 psi. In some embodiments, the material stored within source 50 comprises a pressure of at least about 700 psi. In some embodiments, the material stored within source 50 comprises a coolant or refrigerant, such as, for example, nitrous oxide ($N_2O$). In some embodiments, the nitrous oxide is stored within source 50 as a liquid. In some embodiments, the material stored within source 50 comprises other cryogens and/or liquefied gases, such as, for example, liquid nitrogen and/or liquid helium.

Instrument 12 includes a pressure monitor 62 positioned outside of passageway 26 such that pressure monitor 62 is accessible and/or viewable by a medical practitioner. Pressure monitor 62 comprises a conduit 64 comprising an end 66 that extends through handle 55 and is positioned in passageway 26 and an opposite end 68 positioned within chamber 48. In some embodiments, conduit 64 is directly coupled shaft 26 such that an outer surface of conduit 64 engages the outer surface of shaft 26 and/or conduit 64 extends parallel to axis C. In some embodiments, conduit 64 is removable from shaft 26 and/or is movable relative to shaft 26. Conduit 64 comprises an inner surface defining a channel that is in communication with pressure monitor 62. End 68 comprises an opening 70 that is in communication with the channel defined by the inner surface of conduit 64 such that pressure within chamber 48 can be detected by pressure monitor 62. In some embodiments, pressure monitor 62 includes a display configured to provide a visualization of the pressure within chamber 48. In some embodiments, pressure monitor 62 comprises audio and/or visual components, such as, for example lights or speakers configured to provide alerts when pressure within chamber 48 reaches and/or exceeds a selected threshold pressure. For example, a medical practitioner may preset pressure monitor 62 to provide an alert if and when pressure within chamber 48 reaches and/or exceeds 700 psi, for example, to avoid overinflating balloon 40 and/or rupturing balloon 40. As a further example, a medical practitioner may preset pressure monitor 62 to provide an alert if and when pressure within chamber 48 reaches and/or drops below 10 psi, for example, to indicate when pressure within chamber 48 decreases to a selected threshold.

Instrument 12 comprises a variable exhaust valve 72 extending through handle 55 such that valve 72 is in communication with passageway 26. Valve 72 is configured to regulate pressure within chamber 48. In some embodiments, valve 72 is in communication with pressure monitor 62. Valve 72 is configured to open when pressure within chamber 48 reaches a first selected threshold pressure and to close when pressure within chamber 48 drops to a second selected threshold pressure. For example, valve 72 may be preset to open when pressure within chamber 48 reaches a first selected threshold pressure, such as, for example, 700 psi. When valve 72 is open, pressure within chamber 48 decreases. Pressure within chamber 48 decreases to a second selected threshold pressure, such as, for example, 10 psi, thus causing valve 72 to close. When valve 72 is closed, pressure within chamber 48 remains constant.

In some embodiments, instrument 12 comprises a thermocouple 74 disposed in lumen 34 configured to detect temperature within chamber 48. In some embodiments, thermocouple 74 comprises an end 76 coupled to handle 55 and an opposite end 78 positioned in a portion of lumen 34 that is positioned within chamber 48 such that thermocouple 74 can detect temperature within chamber 48. In some embodiments, thermocouple 74 is coaxial with axis C. In some embodiments, thermocouple 74 is removable from lumen 34.

In assembly, operation and use, surgical system 10, similar to that described above, is employed, for example, with a minimally invasive surgical procedure for spinal and neurosurgical applications with a patient, as shown in FIGS. 4-9. For example, during spine surgery, a surgeon will make an incision in the skin of a patient's back over vertebrae to be treated. One or more hollow instruments, such as, for example, dilators may be employed to gradually separate the muscles and create a portal to a surgical site, such as, for example, a fractured bone, such as, for example, a fractured and/or collapsed vertebral body VB. In some embodiments, the incision is about 1 cm (about ⅓ inch) in length.

Instrument 12 is positioned adjacent a surgical site over the incision. Instrument 12 is passed through the incision and positioned adjacent vertebral body VB. Instrument 12 is positioned relative to vertebral body VB such that balloon 40 is positioned within vertebral body VB, with chamber 48 in the collapsed orientation, as shown in FIG. 4. When balloon 40 is positioned within vertebral body VB, valve 72 is closed and is preset to open when pressure within chamber 48, as detected by pressure monitor 62, reaches a first selected threshold pressure, such as, for example, a pressure within a range of about 50 psi to about 700 psi. Valve 72 is also preset to close when pressure within chamber, as detected by pressure monitor 62, drops to a second threshold pressure, such as for example, a pressure within a range of about 5 psi to about 15 psi. In some embodiments, a guide wire GW is inserted through opening 36 and into lumen 34 such that a tip T of guide wire GW engages tissue, such as, for example, bone, as shown in FIG. 4. Instrument 12 is slid along guide wire GW to position instrument 12 such that balloon 40 is positioned within vertebral body VB.

Figures 6, 7:
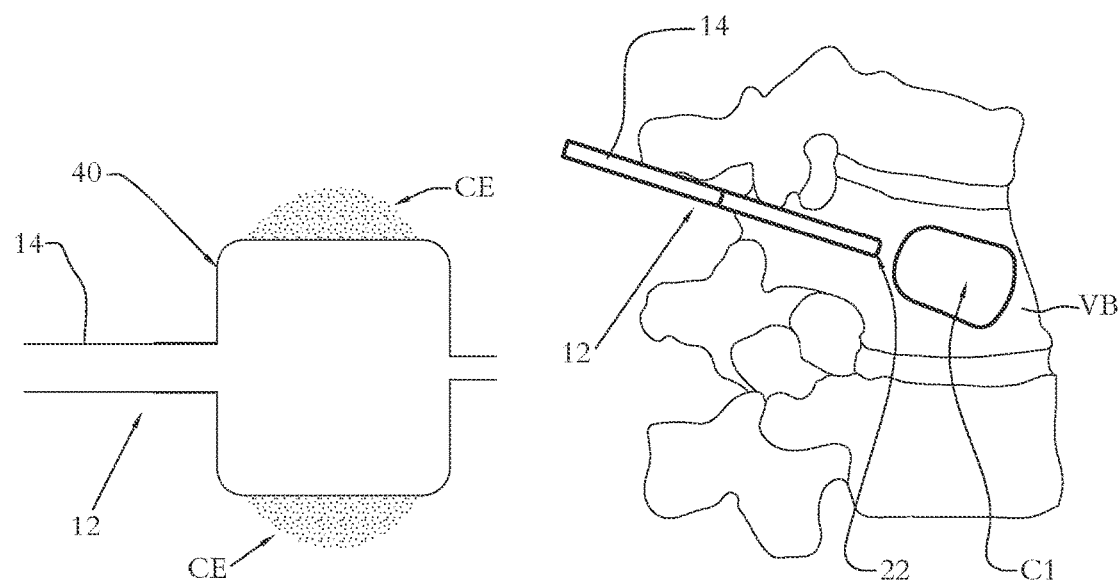
FIG. 6 is a plan view of components shown in FIG. 1, used in connection with a surgical procedure.
FIG. 7 is a plan view of components shown in FIG. 1, used in connection with a surgical procedure.

An inflation and/or filler material M, such as, for example, pressurized liquid nitrous oxide is delivered from source 50 through inlet 52 in the direction shown by arrow D such that pressurized liquid nitrous oxide M exits opening 58 for disposal within chamber 48. Pressurized liquid nitrous oxide M continues to be delivered into chamber 48 until pressure within chamber 48 reaches the first selected threshold pressure. As pressure in chamber 48 reaches the first selected threshold pressure, chamber 48 moves from the unexpanded or uninflated orientation shown in FIG. 4 to the expanded or inflated orientation shown in FIG. 5. As chamber 48 moves from the unexpanded or uninflated orientation to the expanded or inflated orientation, balloon 40 applies an outward force on vertebral body VB so as to raise vertebral body VB and return it to its normal position. As balloon 40 applies an outward force on vertebral body VB, balloon 40 compacts soft, inner bone against the outer surface of balloon 40 so as to create a cavity C1 within vertebral body VB, as shown in FIGS. 5 and 7.

Chamber 48 is filled with pressurized liquid nitrous oxide M until pressure within chamber 48 reaches the first selected threshold pressure. When pressure within chamber 48 reaches the first selected threshold pressure, valve 72 opens. When valve 72 opens, nitrous oxide M moves through passageway 22 in the direction shown by arrow E such that nitrous oxide M exits instrument 12 through valve 72 to reduce pressure within chamber 48. Valve 72 remains open until pressure within chamber 48 reaches the second selected threshold pressure. When pressure within chamber 48 reaches the second selected threshold pressure, valve 72 closes, thus preventing nitrous oxide M from exiting instrument 12 through valve 72 and maintaining the pressure within chamber 48 at the second selected threshold pressure. The pressure difference between the first selected threshold pressure and the second selected threshold pressure causes nitrous oxide M to evaporate, thus producing cold energy CE. Cold energy CE is transmitted through the wall of balloon 40 such that cold energy CE acts on nerves within vertebral body VB to denervate and/or otherwise numb the nerves, as shown in FIG. 6.

In some embodiments, source 50 is in communication pressure monitor 62 such that when pressure monitor 62 detects that pressure within chamber 48 reaches the first selected threshold pressure, pressure monitor 62 sends a signal to source 50 causing a pump of source 50 to stop pumping nitrous oxide M. In some embodiments, source 50 is in communication pressure monitor 62 via one or more wires that connect source 50 with pressure monitor 62. In some embodiments, source 50 includes a pump that is turned on and off manually, based upon the pressure within chamber 48, as identified by a medical practitioner upon viewing and/or hearing pressure monitor 62. For example, a medical practitioner may turn the pump of source 50 off when he or she identifies that pressure within chamber 48 reached the first selected threshold pressure to stop the pump from pumping nitrous oxide M into chamber 48. In some embodiments, valve 72 is in communication with pressure monitor 62 such that when pressure monitor 62 detects that pressure within chamber 48 reaches the first selected threshold pressure, pressure monitor 62 sends a signal to valve 72 causing valve 72 to open. In some embodiments, valve 72 is in communication with pressure monitor 62 via one or more wires that connect pressure monitor 62 with valve 72. Likewise, when pressure monitor 62 detects that pressure within chamber 48 reaches the second selected threshold pressure, pressure monitor 62 sends a signal to valve 72 causing valve 72 to close. In some embodiments, valve 72 is opened and closed manually when a medical practitioner identifies, via pressure monitor 62, that pressure within chamber 48 reaches the first selected threshold pressure or the second selected threshold pressure.

Once the nerves within vertebral body VB are sufficiently denervated and/or numbed, valve 72 is opened, causing nitrous oxide M within chamber 48 to move through passageway 22 in the direction shown by arrow E and exit instrument 12 via valve 72. As nitrous oxide M exits instrument 12, chamber 48 returns to the unexpanded or uninflated orientation shown in FIG. 2. In some embodiments, shaft 26 is slidably disposed within passageway 22 such that moving shaft 26 axially along axis C in the direction shown by arrow E until at least a portion of balloon 40 is disposed within passageway 22, as shown in FIG. 7. Instrument 12 is removed from vertebral body VB with balloon 40 disposed in passageway 22 to reduce the maximum width and/or diameter of instrument 12 to facilitate removal thereof. In some embodiments, instrument 12 is removed without balloon 40 being positioned in passageway 22.

Figure 8:
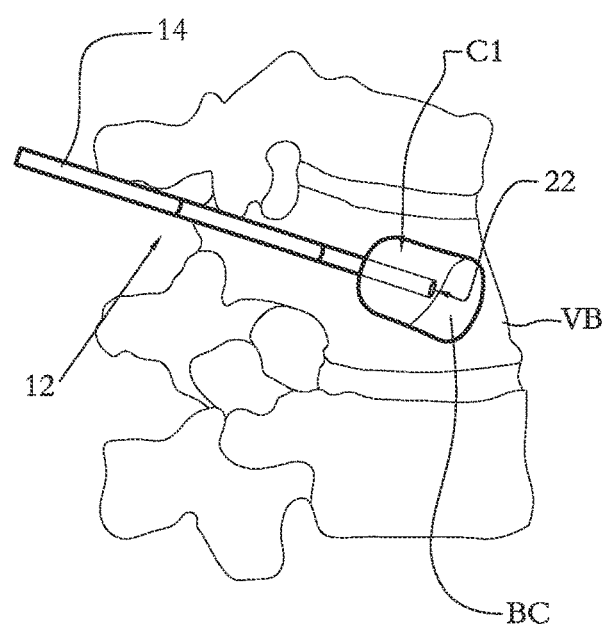
FIG. 8 is a plan view of components shown in FIG. 1, used in connection with a surgical procedure.
Figure 9:
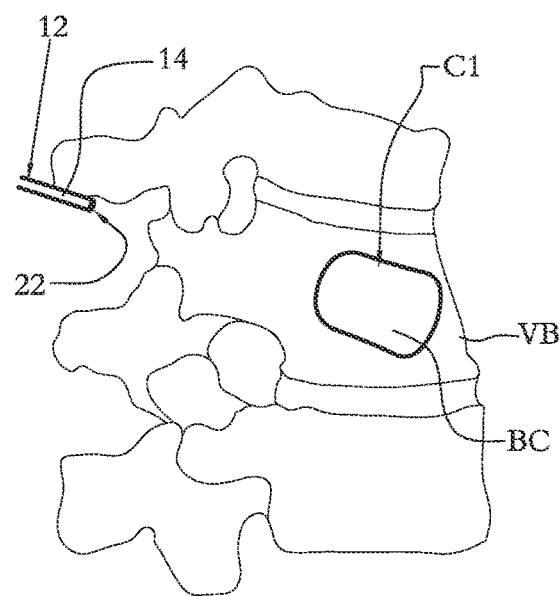
FIG. 9 is a plan view of components shown in FIG. 1, used in connection with a surgical procedure.

An instrument, such as, for example, instrument 12 is introduced into the surgical site and positioned adjacent cavity C1. A material, such as, for example, bone cement BC is delivered through instrument 12 for delivery into cavity C1, as shown in FIG. 8. Bone cement BC is delivered into cavity C1 until a selected amount of bone cement BC is disposed in cavity C1. In some embodiments, bone cement BC is delivered into cavity C1 until bone cement BC completely fills cavity C1, as shown in FIG. 9. After cavity C1 is filled an amount selected by a medical practitioner, instrument 12 is removed from the surgical site, as shown in FIG. 9. In some embodiments, a source of bone cement BC is coupled to tube 26 such that bone cement BC is delivered from the source of bone cement BC through lumen 34 and out of opening 38 for disposal in cavity C1. In some embodiments, the instrument that is used to deliver bone cement BC into cavity C1 is different from instrument 12. In some embodiments, the instrument that is used to deliver bone cement BC into cavity C1 is a cannula. Upon completion of the surgical procedure, instrument 12 and/or the instrument that is used to deliver bone cement BC into cavity C1 is removed from the surgical site.

In some embodiments, system 10 includes at least two instruments 12, which may be used simultaneously in the method discussed above. In one embodiment, a first instrument 12 is positioned adjacent a first side of vertebral body VB such that balloon 40 of the first instrument 12 is positioned within the first side of vertebral body. A second instrument 12 is positioned adjacent a second side of vertebral body VB opposite the first side of vertebral body VB such that balloon 40 of the second instrument 12 is positioned within the second side of vertebral body VB. Balloons 40 of the first and second instruments 12 are inflated with pressurized liquid nitrous oxide in the manner discussed above such that the first and second instruments 12 each restore the height of a respective side of vertebral body VB. Valves 72 on each of the first and second instruments 12 open when pressure within a respective chamber 48 reaches a first selected threshold pressure and the first and second instruments 12 each create a cavity similar to cavity C1. Valves 72 on each of the first and second instruments 12 when pressure within a respective chamber 48 drops to a second selected threshold pressure. As the pressure within chambers 48 drops to the second selected threshold pressure, the difference in pressure between the first selected threshold pressure and the second selected threshold pressure causes nitrous oxide M to evaporate, thus creating cold energy. Balloons 40 and/or the first and second instruments 12 may be removed from vertebral body VB once nerves in vertebral body VB are sufficiently denervated and/or numbed. The cavities created by the first and second instruments 12 may then be filled with bone cement BC in the manner discussed above.

Instrument 12 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument, comprising:
   an outer shaft extending along a longitudinal axis between a first end of the outer shaft and an opposite second end of the outer shaft, the outer shaft comprising an inner surface defining a passageway;
   an inner shaft disposed within the passageway, the inner shaft extending between a first end of the inner shaft and an opposite second end of the inner shaft, the inner shaft comprising an inner surface defining a lumen;
   an expandable structure having a first end coupled to the second end of the outer shaft and an opposite second end coupled to the second end of the inner shaft, the expandable structure comprising an inner surface defining a chamber, the inner shaft being movably disposed within the passageway such that moving the inner shaft axially along the longitudinal axis positions at least a portion of the expandable structure within the passageway;
   a delivery shaft comprising a first end positioned within the passageway and a second end positioned within the chamber, the delivery shaft comprising an inner surface defining a channel configured to deliver a coolant out of an opening in the second end of the delivery shaft and into the chamber to move the expandable structure from an unexpanded configuration to an expanded configuration; and a variable exhaust valve in communication with the passageway configured to regulate pressure within the chamber.

2. The surgical instrument as recited in claim 1, further comprising:

a pressure monitor; and a coolant source comprising a supply of the coolant, wherein the pressure monitor is configured to send a signal to the coolant source to turn a pump of the coolant surface off when pressure within the chamber reaches a selected threshold pressure.

3. The surgical instrument as recited in claim 2, wherein the coolant source is in communication with the channel.

4. The surgical instrument as recited in claim 2, wherein the pressure monitor comprises a first end positioned in the passageway and a second end positioned in the chamber.

5. The surgical instrument as recited in claim 2, wherein the coolant source is in communication with the channel.

6. A surgical method comprising:

providing the surgical instrument of claim 1;

creating an incision;

creating a surgical pathway from the incision to cancellous bone;

positioning the expandable structure within the cancellous bone;

delivering the coolant into the chamber to move the expandable structure from the unexpanded configuration to the expanded configuration to create a cavity within the cancellous bone; and decreasing pressure within the chamber to create cold energy that denervates the cancellous bone.

7. The method as recited in claim 6, wherein:

delivering the coolant into the chamber comprises increasing pressure within the chamber to a first pressure to create the cavity;

decreasing pressure within the chamber comprises adjusting pressure within the chamber from the first pressure to a second pressure that is less than the first pressure to create the cold energy; and the first pressure is greater than about 50 psi and the second pressure is about 10 psi.

8. The method as recited in claim 7, wherein the coolant is maintained within the chamber as pressure within the chamber is decreased.

9. The method as recited in claim 6, wherein decreasing pressure within the chamber comprises adjusting the variable exhaust valve.

10. The method as recited in claim 6, further comprising: moving the expandable structure from the expanded configuration to the unexpanded configuration; removing the surgical instrument from the cavity; and filling the cavity with bone cement.

11. A surgical instrument, comprising:

an outer shaft defining a longitudinal axis, the outer shaft comprising an inner surface defining a passageway;

an inner shaft movably disposed within the passageway, the inner shaft comprising an inner surface defining a lumen;

a balloon having a first end coupled to the outer shaft and an opposite second end coupled to the inner shaft, the balloon defining a chamber;

a delivery shaft comprising a first end positioned within the passageway and a second end positioned within the chamber, the delivery shaft defining a channel configured to deliver a coolant out of the delivery shaft and into the chamber to inflate the balloon; and a variable exhaust valve in communication with the passageway configured to regulate pressure within the chamber, wherein the inner shaft is movable relative to the outer shaft to move the balloon from a first orientation in which the balloon is positioned entirely outside of the passageway and a second orientation in which at least a portion of the expandable structure within the passageway.

12. The surgical instrument as recited in claim 11, further comprising:

a pressure monitor; and a coolant source comprising a supply of the coolant, wherein the pressure monitor is configured to send a signal to the coolant source to turn a pump of the coolant surface off when pressure within the chamber reaches a selected threshold pressure, wherein the pressure monitor comprises a first end positioned in the passageway and a second end positioned in the chamber, and wherein the coolant source is in communication with the channel.

13. A surgical instrument, comprising:

an outer shaft defining a longitudinal axis, the outer shaft comprising an inner surface defining a passageway;

an inner shaft movably disposed within the passageway, the inner shaft comprising an inner surface defining a lumen;

a balloon having a first end coupled to the outer shaft and an opposite second end coupled to the inner shaft, the balloon defining a chamber;

a delivery shaft defining a channel configured to deliver a coolant out of the delivery shaft and into the chamber to inflate the balloon, wherein the inner shaft is movable relative to the outer shaft to move the balloon from a first orientation in which the balloon is positioned entirely outside of the passageway and a second orientation in which at least a portion of the expandable structure within the passageway.

14. The surgical instrument as recited in claim 13, further comprising:

a pressure monitor; and a coolant source comprising a supply of the coolant, wherein the pressure monitor is configured to send a signal to the coolant source to turn a pump of the coolant surface off when pressure within the chamber reaches a selected threshold pressure, wherein the pressure monitor comprises a first end positioned in the passageway and a second end positioned in the chamber, and wherein the coolant source is in communication with the channel.

* * * * *